United States Patent
Li

(10) Patent No.: US 11,623,010 B2
(45) Date of Patent: Apr. 11, 2023

(54) PHARMACEUTICAL CARRIER IN THE PREPARATION OF AN ANTI-DIABETIC PHARMACEUTICAL COMPOSITION AND METHODS FOR TREATMENT

(71) Applicants: BEIJING RONGXIANG INSTITUTE OF REGENERATIVE MEDICINE CO., LTD., Beijing (CN); Li Li, Beijing (CN)

(72) Inventor: Li Li, Beijing (CN)

(73) Assignees: Li Li, Beijing (CN); BEIJING RONGXIANG INSTITUTE OF REGENERATIVE MEDICINE CO., LTD., Beijing (CN)

( * ) Notice: Subject to any disclaimer, the term of this patent is extended or adjusted under 35 U.S.C. 154(b) by 80 days.

(21) Appl. No.: 16/553,056

(22) Filed: Aug. 27, 2019

(65) Prior Publication Data
US 2020/0069806 A1  Mar. 5, 2020

(51) Int. Cl.
| | |
|---|---|
| *A61K 47/54* | (2017.01) |
| *A61K 47/44* | (2017.01) |
| *A61P 1/16* | (2006.01) |
| *A61K 31/56* | (2006.01) |
| *A61K 31/4375* | (2006.01) |

(52) U.S. Cl.
CPC ............ *A61K 47/542* (2017.08); *A61K 47/44* (2013.01); *A61P 1/16* (2018.01); *A61K 31/4375* (2013.01); *A61K 31/56* (2013.01)

(58) Field of Classification Search
CPC .... A61K 31/56; A61K 31/4375; A61K 47/44; A61K 47/542; A61P 1/16
See application file for complete search history.

(56) References Cited

U.S. PATENT DOCUMENTS 6,991,813 B2  1/2006  Xu

FOREIGN PATENT DOCUMENTS

| CN | 1090179 A | 8/1994 |
|---|---|---|
| CN | 1145779 A | 9/1995 |
| CN | 100444844 C | 12/2008 |
| CN | 100548382 C | 10/2009 |
| CN | 106551942 A | 4/2017 |
| EP | 0 763 362 A2 | 3/1997 |
| WO | WO 03/037360 A1 | 5/2003 |

OTHER PUBLICATIONS

Li, M., et al; Integrative analysis of metabolome and gut microbiota in diet-induced hyperlipidemic rats; J.Transl. Med.; vol. 14,No. 1; Aug. 2016; 13 pgs.
Pan, et al; A combination of berberine and y-oryzanol for hyperlipidemia therapy: An hypothesis; African Jour. Pharmacy and Pharmacology; vol. 6(6);Feb. 15, 2012; pp. 355-358.
European Patent Office; Communication; EP Search Report; EP Appl. No. 19193839; dated Jan. 28, 2020; 4 pgs.
European Patent Office; Communication pursuant to Article 94(3) EPC; Application No. 19193839.8 dated Nov. 5, 2020; 15 pgs.

*Primary Examiner* — Adam C Milligan
(74) *Attorney, Agent, or Firm* — Kilpatrick Townsend & Stockton LLP

(57) ABSTRACT

The present invention relates to the use of a pharmaceutical carrier in the preparation of anti-diabetic pharmaceutical composition. In particular, the present invention relates to the use of a pharmaceutical carrier in the preparation of anti-diabetic pharmaceutical composition, wherein the pharmaceutical carrier consists of well-mixed sesame oil and beeswax, the anti-diabetic pharmaceutical composition comprises oryzanol and berberine hydrochloride as active ingredients; wherein the oryzanol is present in an amount of 1-5% by weight, the berberine hydrochloride is present in an amount of 5-50% by weight, the beeswax is present in an amount of 1-20% by weight, and the sesame oil is present in an amount of 40-85% by weight, relative to the total weight of the pharmaceutical composition. The present invention further relates to an anti-diabetic pharmaceutical composition as above, which is subjected to compressing, rinsing, drying and screening, and packaged into vial to obtain a product in soft capsule dosage form. The product has advantages such as stable control of blood glucose, lowering the level of blood glucose and blood lipid, protecting liver function, as well as low irritation on gastrointestinal tract.

23 Claims, No Drawings

PHARMACEUTICAL CARRIER IN THE PREPARATION OF AN ANTI-DIABETIC PHARMACEUTICAL COMPOSITION AND METHODS FOR TREATMENT

CROSS-REFERENCE TO RELATED APPLICATIONS

This application claims priority to Chinese Application No. CN 201811000758.X, filed Aug. 29, 2018, the disclosure of which is hereby incorporated by reference in its entirety for all purposes.

FIELD OF THE INVENTION

The present invention relates to the field of medical technology, especially relates to the use of a pharmaceutical carrier comprising sesame oil and beeswax in the preparation of an anti-diabetic pharmaceutical composition that comprises oryzanol and berberine hydrochloride as active ingredients. The present invention also relates to the use of said anti-diabetic pharmaceutical composition for treating diabetes, in particular type II diabetes.

BACKGROUND OF THE INVENTION

Diabetes is a group of metabolic diseases characterized by chronic hyperglycemia. Diabetes is caused by islet dysfunction, defects in insulin secretion and/or impaired biological effect of insulin due to the effects of various pathogenic factors (such as genetic factors, immune dysfunction, microbial infection and toxins thereof, free radical toxins and mental factors) on the body. In addition to abnormal metabolism of carbohydrate, there are a series of abnormal metabolism such as abnormal metabolism of protein, fat, water and electrolytes presented in a diabetes patient. Diabetes is characterized by a long-term hyperglycemia which causes chronic damage and dysfunction of various tissues, in particular eye, kidney, heart, blood vessel and nerve.

Diabetes due to lack of insulin or insufficient insulin secretion is referred to as type I diabetes. Diabetes due to insulin resistance that causes inefficient bio-availability of insulin is referred to as type II diabetes.

Diabetes is a growing global pandemic. About 400 million adults worldwide have been affected by diabetes by the year of 2015, of which about 100 million are in China. The sustained high level of glucose can lead to complications of diabetes such as heart disease, stroke, kidney failure, lower limb amputation and blindness. Therefore, the control of blood glucose is an urgent goal for patients with type II diabetes.

According to the mechanism, hypoglycemic drugs can be divided into several major categories such as insulin and its analogues, sulfonylurea secretagogues, metformins, alpha-glucosidase inhibitors, thiazolidinedione derivative sensitizers, phenyl anisic acid derivative secretagogues, GLP-1 receptor agonists, DPP-4 enzyme inhibitors, and Chinese traditional medicines.

Berberine hydrochloride provides a hypoglycemic effect by promoting the recovery and proliferation of islet β cells, increasing insulin release, inhibiting gluconeogenesis and promoting glycolysis; an anti-arrhythmia and hypotensive effect by competitively blocking alpha-adrenergic receptors and enhancing atrial contractility; and an effect of treating ulcerative gastrointestinal inflammation by protecting the gastrointestinal mucosal from bacterial infection.

Oryzanol is present in rice bran oil, and is a mixture of ferulates mainly consisted of triterpene (alkenyl) alcohol. Oryzanol mainly acts on the autonomic nervous system and endocrine center of the diencephalon. Oryzanol can regulate autonomic nerve function, reduce endocrine balance disorder, and improve symptoms of neurological disorders. Oryzanol also has various physiological functions such as lowering blood lipid, lowering liver lipid, preventing lipid from oxidation and anti-oxidation. In addition, oryzanol also has an anti-arrhythmia effect, and can reduce myocardial excitability by regulating autonomic function. The lipid-lowering effect of oryzanol can also improve the blood supply to the myocardium and improve sleep.

Patent publication No. CN100548382C discloses a pharmaceutical carrier and a method for preparing the same. The pharmaceutical carrier consists of well-mixed edible oil and beeswax, and the edible oil can be sesame oil. The pharmaceutical carrier can be used as a regulator for regeneration of gastrointestinal tissue in treating gastrointestinal diseases.

The present inventor discovered that the above pharmaceutical carrier can be applied to control blood glucose in a diabetic patient, and the pharmaceutical carrier also plays a better role in controlling blood glucose when combined with the carried drugs so as to overcome the possible irritation effect of the drugs on the gastrointestinal tract. In particular, the above pharmaceutical carrier in combination with berberine hydrochloride and oryzanol can be effectively used for treating diabetes, and can overcome the possible side effects of these drugs such as irritation on the gastrointestinal tract.

SUMMARY OF THE INVENTION

The present inventor disperses berberine hydrochloride and oryzanol into a medium consisting of sesame oil and beeswax to treat diabetes, particularly type II diabetes.

Therefore, one object of the present invention is to provide the use of a pharmaceutical carrier in the preparation of an anti-diabetic pharmaceutical composition, wherein the pharmaceutical carrier consists of well-mixed sesame oil and beeswax, the anti-diabetic pharmaceutical composition comprises oryzanol and berberine hydrochloride as active ingredients; the oryzanol is present in an amount of 1-5% by weight, the berberine hydrochloride is present in an amount of 5-50% by weight, the beeswax is present in an amount of 1-20% by weight, and the sesame oil is present in an amount of 40-85% by weight, relative to the total weight of the pharmaceutical composition.

The present invention further provides an anti-diabetic pharmaceutical composition, characterized in that the composition comprises a pharmaceutical carrier consisting of well-mixed sesame oil and beeswax as well as oryzanol and berberine hydrochloride as active ingredients; wherein the oryzanol is present in an amount of 1-5% by weight, the berberine hydrochloride is present in an amount of 5-50% by weight, the beeswax is present in an amount of 1-20% by weight, and the sesame oil is present in an amount of 40-85% by weight, relative to the total weight of the pharmaceutical composition.

In a preferred embodiment of the present invention, in the anti-diabetic pharmaceutical composition of the present invention, the beeswax is present in an amount of 2-10% by weight, and the sesame oil is present in an amount of 50-80% by weight, relative to the total weight of the pharmaceutical composition.

In another preferred embodiment of the present invention, in the anti-diabetic pharmaceutical composition of the present invention, the oryzanol is present in an amount of 2-4% by weight, the berberine hydrochloride is present in an amount of 15-30% by weight, the beeswax is present in an amount of 3-6% by weight, and the sesame oil is present in an amount of 60-75% by weight, relative to the total weight of the pharmaceutical composition. Preferably, the weight ratio of beeswax to sesame oil is from 1:25 to 1:10. The optimal weight ratio of oryzanol to berberine hydrochloride is 1.10.

In another preferred embodiment of the present invention, in the anti-diabetic pharmaceutical composition of the present invention, the weight ratio of beeswax to sesame oil is from 1:40 to 1:5, and preferably from 1:25 to 1:10.

In another preferred embodiment of the present invention, in the anti-diabetic pharmaceutical composition of the present invention, the weight ratio of oryzanol to berberine hydrochloride is 1:10.

The beeswax used in the present invention is a purified granule. The beeswax is yellow, yellowish brown or yellowish white, opaque or slightly transparent, and has a smooth surface. The beeswax is light in weight, waxy, and has a granular texture on fracture surface. The beeswax can be softened by hand kneading. The beeswax has a melting point of 62 to 65° C.

In a preferred embodiment, the beeswax of the present invention is homogeneously dispersed in the sesame oil, and can form microcrystals, the length of the microcrystal is from 0.1 to 100 μm, preferably from 5 to 70 μm, and more preferably from 10 to 50 μm.

The sesame oil used in the present invention can be a machine-made sesame oil, ground sesame oil or common sesame oil.

The berberine hydrochloride of the present invention is derived from an extract of *Phellodendron Amurense Rupr.* or *Berberis sargentiana Schneid*. The extraction method of berberine hydrochloride is known in the art. Generally, for example, the bark of *Phellodendron Amurense Rupr.* is dried, pulverized into a coarse powder, and added with lime milk; the mixture is stirred well followed by cold quenching, and extracted with saturated lime water to obtain an extract; the extract is acidified with hydrochloric acid, and precipitated to obtain crude berberine hydrochloride. The crude berberine hydrochloride is subjected to dissolution in hot water, precipitation with lime water, acidification and crystallization twice, and then purified with methanol, separated, dried and pulverized to obtain berberine hydrochloride.

The oryzanol of the present invention is derived from an extract of rice bran oil, a by-product obtained during the processing of rice (*Oryza sativa L.*) seed. The extraction method of oryzanol is known in the art. Generally, the crude rice bran oil is alkali-refined twice; the oryzanol-containing nigre is pre-saponified and fully saponified, followed by cooling to obtain the lipoid; the oryzanol is precipitated from the methanol solution by adding weak acid or weak acid salt, and the soap methanol solution is removed by cooling to obtain crude oryzanol; a series of purification processes are then carried out to obtain an oryzanol powder.

In another aspect, the present invention provides a method for preparing the anti-diabetic pharmaceutical composition of the present invention, comprising the following steps of:

1) heating the sesame oil at a temperature above the melting point of the beeswax;
2) adding the beeswax and stirring well;
3) cooling slightly followed by adding oryzanol and berberine hydrochloride into the mixture obtained in step 2) with stirring;
4) cooling the mixture obtained in step 3) to room temperature followed by grinding with colloid mill or homogenous grinding to enable oryzanol and berberine hydrochloride to be homogeneously dispersed in the medium consisting of sesame oil and beeswax;
5) subjecting the mixture to vacuum degassing to obtain the content;
6) subjecting the content to compressing, rinsing, drying and screening, and filling it into a vial to obtain the product in soft capsule dosage font.

In the method of the present invention, in step 1), the sesame oil is preferably heated to a temperature of 90° C. to 180° C., more preferably 100° C. to 170° C., and most preferably 110° C. to 160° C.

In the method of the present invention, in step 2), the sesame oil and beeswax are continuously stirred at a temperature of 90° C. to 180° C., preferably 100° C. to 170° C., and most preferably 110° C. to 160° C. for 5 to 60 minutes, preferably 10 to 40 minutes, and most preferably 15 to 30 minutes.

In the method of the present invention, in step 3), the mixture is cooled under stirring to 40 to 90° C., and preferably to 60 to 80° C. followed by adding oryzanol; and the mixture is cooled under stirring to a temperature of not higher than 60° C., and preferably to room temperature followed by adding berberine hydrochloride.

In the method of the present invention, in step 4), the mixture is homogeneously dispersed with colloid mill or homogenous grinding at room temperature to obtain a homogeneous formulation.

In an embodiment of the present invention, the method for preparing the anti-diabetic pharmaceutical composition of the present invention comprises the following steps of:

1) heating the sesame oil (40-85% by weight) to a temperature of 90° C. to 180° C.;
2) adding the beeswax (1-20% by weight) to the heated sesame oil obtained in step 1), and stirring for 5 to 60 minutes;
3) cooling the mixture obtained in step 2) with stirring (20 to 350 rpm) to a temperature of 40 to 90° C. followed by adding oryzanol (1-5% by weight); and cooling the mixture to room temperature followed by adding berberine hydrochloride;
4) cooling the mixture obtained in step 3) under stirring (20 to 350 rpm) to room temperature followed by grinding with colloid mill or homogenous grinding to enable the mixture to be homogeneously dispersed;
5) subjecting the mixture to vacuum degassing to obtain the content;
6) subjecting the content to compressing, rinsing, drying and screening, and filling it into a vial to obtain the product in soft capsule form.

In another aspect, the present invention provides the use of the pharmaceutical composition according to the present invention in the preparation of a medicament for treating diabetes, in particular type II diabetes. The pharmaceutical composition can overcome side effects, such as irritation of the active ingredients on the gastrointestinal tract.

In addition to the above essential pharmaceutical carrier and active ingredients, the pharmaceutical composition according to the present invention can further comprise a pharmaceutically acceptable vehicle, adjuvant or diluent, such as a filler, disintegrant, lubricant, suspending agent, binder, sweetener, flavoring agent, preservative, matrix and the like. The examples of filler include starch, pre-gelatinized starch, lactose, mannitol, chitin, microcrystalline cellulose, sucrose and the like. The examples of disintegrant include starch, pre-gelatinized starch, microcrystalline cellulose, sodium carboxymethyl starch, crosslinked polyvinylpyrrole, low substituted hydroxypropyl cellulose, croscarmellose sodium and the like. The examples of lubricant include magnesium stearate, sodium lauryl sulfate, talc, silica and the like. The examples of suspending agent include polyvinylpyrrolidone, microcrystalline cellulose, sucrose, agar, hydroxypropyl methylcellulose and the like. The examples of binder include starch pulp, polyvinylpyrrolidone, hydroxypropyl methylcellulose and the like. The compositions of the present invention can be prepared by any method known in the art to provide a rapid, sustained or slow release of the active ingredients after administration to a patient.

In addition to the soft capsule mentioned above, the pharmaceutical composition according to the present invention can be formulated depending on the particular mode of administration into various formulations well known in the art, such as a tablet, hard capsule, syrup, elixir, sachet, granule, emulsion, ointment, gel, balm, plaster, paste, suppository, cream and the like.

The anti-diabetic pharmaceutical composition of the present invention is prepared with a pharmaceutical carrier consisting of sesame oil and beeswax; as well as oryzanol and berberine hydrochloride as active ingredients. It not only has an excellent anti-diabetic efficacy, but also overcomes side effects such as irritation of the active ingredients on the gastrointestinal tract.

DETAILED DESCRIPTION OF THE INVENTION

The present invention is further illustrated in detail by the following examples. These examples of the present invention are merely for the purpose of illustrating the technical solutions of the present invention, and are not intended to limit the scope of the present invention.

Test materials: The beeswax was purchased from Anguo Runde Pharmaceutical Co., Ltd. (produced by Cangzhou Zhuohang Beeswax Co., Ltd.). The sesame oil was purchased from Langfang Mebo Pharmaceutical Co., Ltd. The oryzanol was purchased from Zhejiang Delekang Food Co., Ltd. The berberine hydrochloride was purchased from Sichuan Xieli Pharmaceutical Co., Ltd. The colloid mill is JMS-80B colloid mill, which is manufactured by Langfang General Motors Machinery Manufacture Co., Ltd.

EXAMPLES

Example 1

3750 g of sesame oil was heated to 160° C., added with 150 g of beeswax, and stirred for 15 minutes. The mixture was cooled to 80° C., added with 100 g of oryzanol, and stirred for 15 minutes. The mixture was cooled to 80° C., added with 1000 g of berberine hydrochloride, and cooled to room temperature. The mixture was ground with the colloid mill twice, and subjected to vacuum degassing. The mixture was formulated into soft capsule, and the specification of the content was 0.5 g per capsule.

Example 2

7500 g of sesame oil was heated to 110° C., added with 600 g of beeswax, and stirred for 30 minutes. The mixture was cooled to 60° C., and added with 400 g of oryzanol and 1500 g of berberine hydrochloride. The mixture was stirred for 30 minutes, and cooled to room temperature. The mixture was homogenized, and subjected to vacuum degassing. The mixture was formulated into soft capsule, and the specification of the content was 1000 mg per capsule.

Example 3

6000 g of sesame oil was heated to 130° C., added with 600 g of beeswax, and stirred for 30 minutes. The mixture was cooled to 70° C., and added with 400 g of oryzanol and 3000 g of berberine hydrochloride. The mixture was stirred for 30 minutes, and cooled to room temperature. The mixture was homogenized, and subjected to vacuum degassing. The mixture was formulated into soft capsule, and the specification of the content was 1000 mg per capsule.

Example 4

67.5 kg of sesame oil was heated to 140° C., added with 5 kg of beeswax, and stirred for 30 minutes. The mixture was cooled to 80° C., added with 2.5 kg of oryzanol, and stirred for 30 minutes. The mixture was cooled to room temperature, added with 25 kg of berberine hydrochloride, and stirred for 30 minutes. The mixture was homogenized, and subjected to vacuum degassing. The mixture was formulated into soft capsule, and the specification of the content was 1000 mg per capsule.

Test Examples 438 patients (50-82 years-old) with type II diabetes were subjected to a routine examination at hospital or physical examination center before the test, and the examination items included height, weight, BMI, systolic blood pressure, diastolic blood pressure, heart rate, blood routine analysis, urine routine analysis, alanine aminotransferase (ALT), aspartate aminotransferase (AST), γ-aminoacyltransferase, alkaline phosphatase, urea, creatinine, uric acid, fasting blood glucose, 2-hour postprandial blood glucose, glycated hemoglobin, waistline, total cholesterol, low-density lipoprotein cholesterol, triglycerides, high-density lipoprotein cholesterol and the like. For all patients, the fasting blood glucose was higher than 6.1 mmol/L, and the 2-hour postprandial blood glucose was higher than 10.0 mmol/L. Therefore, all patients met the diagnostic criteria for diabetes. The patients were adminstrated with the soft capsules prepared in Example 4 of the present invention three times a day, with two capsules each time. After two months of adminstration, the patients were subjected to a routine examination at hospital or physical examination center again, and the examination items were the same as above.

Test example 1. Effect of the pharmaceutical composition of the present invention on the blood glucose of diabetic patient The control of blood glucose in 438 patients before and after adminstration of the soft capsule prepared in Example 4 of the present invention for two months was analyzed, by self-control method with three indicators being evaluated (fasting blood glucose, 2-hour postprandial blood glucose and glycated hemoglobin).

The values of fasting blood glucose, 2-hour postprandial blood glucose and glycated hemoglobin of the 438 patients before and after adminstration of the soft capsule prepared in Example 4 of the present invention for two months were analyzed, by paired t-test model. The results are shown in Table 1 below. The values of fasting blood glucose, 2-hour postprandial blood glucose and glycated hemoglobin are expressed as mean±standard deviation.

TABLE 1

Comparison of blood glucose indicators in the 438 patients before and after adminstration of the soft capsule prepared in Example 4 of the present invention

|  | Before adminstration | After adminstration |
|---|---|---|
| Fasting blood glucose (mmol/L) | 8.81 ± 2.70 | 7.18 ± 1.91** |
| 2-hour postprandial blood glucose (mmol/L) | 13.98 ± 4.26 | 10.42 ± 3.71** |
| Glycated hemoglobin (%) | 7.84 ± 1.81 | 6.53 ± 1.03** |

Note:
**The indicators (fasting blood glucose, 2-hour postprandial blood glucose and glycated hemoglobin) of the patients after adminstration are significantly lower than that before adminstration (P < 0.01).

As can be seen from Table 1 above, the values of fasting blood glucose, 2-hour postprandial blood glucose and glycated hemoglobin of the patients decreased significantly after adminstration of the soft capsule of the present invention, which has a statistical significance (P<0.01). Moreover, the patients had no gastrointestinal adverse effects and no other discomfort.

Test example 2. Effect of the pharmaceutical composition of the present invention on the blood lipid in diabetic patients The values of total cholesterol, triglycerides and low-density lipoprotein cholesterol (LDL-C) in the serum of 438 patients before and after adminstration of the soft capsule prepared in Example 4 of the present invention for two months were analyzed by paired t-test model. The values of total cholesterol, triglycerides and low-density lipoprotein cholesterol (LDL-C) in serum are expressed as mean±standard deviation. The results are shown in Table 2 below.

TABLE 2

Comparison of blood lipid indicators in the 438 patients before and after adminstration of the soft capsule prepared in Example 4 of the present invention

|  | Before adminstration | After adminstration |
|---|---|---|
| Total cholesterol (mmol/L) | 5.16 ± 1.09 | 4.38 ± 0.84** |
| LDL-C (mmol/L) | 2.93 ± 0.81 | 2.47 ± 0.68** |
| Triglycerides (mmol/L) | 2.61 ± 1.42 | 1.63 ± 1.25** |

Note:
**The indicators (total cholesterol, low-density lipoprotein cholesterol and triglycerides) in the serum of the patients after adminstration of the soft capsule of the present invention are significantly lower than that before adminstration (P < 0.01).

As can be seen from Table 2 above, the values of total cholesterol, low-density lipoprotein cholesterol and triglycerides in the serum of the patients were improved after adminstration of the soft capsule of the present invention, indicating that the adminstration of the soft capsule of the present invention can reduce the blood lipid of diabetic patient to a certain extent, and improve cardiovascular function.

Test example 3. Effect of the pharmaceutical composition of the present invention on the liver function of diabetic patients According to the routine examination reports before adminstration, it is noticed that among the above 438 patients, 57 patients have alanine aminotransferase (ALT) value higher than 40; 43 patients have aspartate aminotransferase (AST) value higher than 40; and 47 patients have γ-aminoacyltransferase value higher than 45. The values of alanine aminotransferase (ALT), aspartate aminotransferase (AST) and γ-aminoacyltransferase of the above patients before and after adminstration of the soft capsule prepared in Example 4 of the present invention for two months were analyzed by paired t-test model.

The values of alanine aminotransferase (ALT), aspartate aminotransferase (AST) and γ-aminoacyltransferase of the above patients are expressed as mean±standard deviation. The results are shown in Table 3 below.

TABLE 3

Comparison of liver function indicators before and after adminstration of the soft capsule prepared in Example 4 of the present invention

|  | Number of patients | Before adminstration | After adminstration |
|---|---|---|---|
| ALT (U/L) | 57 | 72.2 ± 35.6 | 23.5 ± 10.3** |
| AST (U/L) | 43 | 61.6 ± 28.1 | 25.7 ± 8.3** |
| γ-GT (U/L) | 47 | 97.2 ± 53.9 | 48.8 ± 24.3** |

As can be seen from Table 3 above, the values of the indicators of the patients were all improved after adminstration of the soft capsule of the present invention, which has a statistical significance (P<0.01), indicating that the adminstration of the soft capsule of the present invention can improve the liver function of diabetic patients to a certain extent.

Test example 4. Protection effect of the pharmaceutical composition of the present invention on the gastrointestinal tract of diabetic patients Among the 438 patients adminstrated with the soft capsule of the present invention, 37 patients had been adminstrated with commercially available berberine tablets (berberine hydrochloride tablets) and oryzanol tablets for a short or long period of time to control blood glucose before adminstration of the soft capsule of the present invention. Among these patients adminstrated with berberine tablets and oryzanol tablets, some of them had adverse reactions or side effects such as stomach upset, nausea, vomiting, constipation, thirst and the like.

In the patients adminstrated with the soft capsule of the present invention, the gastrointestinal adverse effects such as stomach upset, nausea, vomiting, constipation, thirst and the like almost did not appear due to the excellent stomach mucosa-protecting efficacy of the pharmaceutical carrier which is consisted of sesame oil and beeswax. The comparison of gastrointestinal adverse effects of the 37 patients before and after adminstration of the soft capsule of the present invention is shown in Table 4.

TABLE 4

Number of patients that had gastrointestinal adverse effects after administration of berberine tablets and oryzanol tablets or after adminstration of the soft capsule of the present invention

|  | After adminstration of berberine tablets and oryzanol tablets | After adminstration of the soft capsule of the present invention |
|---|---|---|
| Stomach upset | 12/37 | 1/37 |
| Nausea | 4/37 | 0/37 |
| Vomiting | 3/37 | 0/37 |
| Constipation | 21/37 | 0/37 |
| Thirst | 6/37 | 1/37 |

After combined adminstration of berberine tablets and oryzanol tablets, the diabetic patients can have gastric adverse effects including sour regurgitation, bloating, belching, loss of appetite, feeling to vomit and the like, as well as nausea and vomiting when the adverse effect is severe, which may possibly result from the irritation effect of berberine and oryzanol on the gastrointestinal tract.

As can be seen from the above Table 4, the pharmaceutical carrier consisting of sesame oil and beeswax used in the soft capsule of the present invention has a stomach mucosa-protecting effect, and can relieve and eliminate symptoms of gastric adverse effects caused by the drugs. Moreover, the sesame oil and beeswax in the pharmaceutical carrier of the soft capsule of the present invention has a laxative effect, and can improve intestinal mucosal cell secretory function and intestinal wall muscle cell viability, as well as effectively relieve constipation, especially in the elderly.

In addition, the mental state of most patients was greatly improved after adminstration of the soft capsule of the present invention. These patients stated that they had an improved appetite, physical strength and complexion, and felt that the physical condition was improved significantly than before.

What is claimed is:

1. An anti-diabetic pharmaceutical composition in capsule or tablet form for oral administration, consisting of:
   oryzanol and berberine hydrochloride as active ingredients; and
   a pharmaceutical carrier consisting of well-mixed sesame oil and beeswax;
   wherein, the oryzanol is present in an amount of 1-5% by weight relative to the total weight of the pharmaceutical composition,
   the berberine hydrochloride is present in an amount of 5-50% by weight relative to the total weight of the pharmaceutical composition,
   the beeswax is present in an amount of 1-20% by weight relative to the total weight of the pharmaceutical composition, and
   the sesame oil is present in an amount of 40-85% by weight, relative to the total weight of the pharmaceutical composition within the capsule or tablet; and
   the beeswax forms microcrystals which are homogeneously dispersed in the sesame oil.

2. The anti-diabetic pharmaceutical composition according to claim 1, wherein the beeswax is present in an amount of 2-10% by weight, and the sesame oil is present in an amount of 50-80% by weight, relative to the total weight of the pharmaceutical composition.

3. The anti-diabetic pharmaceutical composition according to claim 1, wherein the oryzanol is present in an amount of 2-4% by weight, the berberine hydrochloride is present in an amount of 15-30% by weight, the beeswax is present in an amount of 3-6% by weight, and the sesame oil is present in an amount of 60-75% by weight, relative to the total weight of the pharmaceutical composition.

4. The anti-diabetic pharmaceutical composition according to claim 1, wherein the weight ratio of beeswax to sesame oil is from 1:40 to 1:5.

5. The anti-diabetic pharmaceutical composition according to claim 1, wherein the weight ratio of oryzanol to berberine hydrochloride is 1:10.

6. The anti-diabetic pharmaceutical composition according to claim 1, wherein the length of the microcrystals are from 0.1 to 100 μm.

7. The anti-diabetic pharmaceutical composition according to claim 1, wherein the sesame oil is a machine-made sesame oil, ground sesame oil or common sesame oil.

8. The anti-diabetic pharmaceutical composition according to claim 1, wherein the anti-diabetic pharmaceutical composition is formulated into a soft capsule.

9. The anti-diabetic pharmaceutical composition according to claim 4, wherein the weight ratio of beeswax to sesame oil is from 1:25 to 1:10.

10. The anti-diabetic pharmaceutical composition according to claim 6, wherein the length of the microcrystals are from 5 to 70 μm.

11. The anti-diabetic pharmaceutical composition according to claim 6, wherein the length of the microcrystals are from 10 to 50 μm.

12. A method for preparing an anti-diabetic pharmaceutical composition according to claim 1, comprising the following steps of:
   1) heating the sesame oil at a temperature above the melting point of the beeswax, the temperature is 90° C. to 180° C.;
   2) adding the beeswax to the heated sesame oil obtained in step 1), and stirring well for 5 to 60 minutes;
   3) cooling the mixture obtained in step 2) by stirring to a temperature of 40° C. -90° C., and followed by adding the oryzanol; and cooling the mixture to a temperature of not higher than 60° C., and followed by adding the berberine hydrochloride;
   4) cooling the mixture obtained in step 3) to room temperature followed by grinding with colloid mill or homogenous grinding to enable the oryzanol and berberine hydrochloride to be homogeneously dispersed in the medium consisting of sesame oil and beeswax;
   5) subjecting the mixture to vacuum degassing to obtain the anti-diabetic pharmaceutical composition in accordance to claim 1.

13. A method of treating diabetes, the method comprising administering to a subject an anti-diabetic pharmaceutical composition according to claim 1.

14. The method according to claim 13, wherein said composition is for an indication selected from a group consisting of: reducing blood lipid, protecting liver function, or protecting the gastrointestinal tract.

15. The method of claim 12, wherein: 1) heating the sesame oil at a temperature above the melting point of the beeswax, wherein the temperature is 100° C. to 170° C.;
   2) adding the beeswax to the heated sesame oil obtained in step 1), and stirring well for 10 to 40 minutes; and
   3) cooling the mixture obtained in step 2) by stirring to a temperature of 60° C. to 80° C. followed by adding the oryzanol.

16. The method of claim 12, wherein: 1) heating the sesame oil at a temperature above the melting point of the beeswax, the temperature is 110° C. to 160° C.;
   2) adding the beeswax to the heated sesame oil obtained in step 1), and stirring well for 15 to 30 minutes; and
   3) cooling the mixture obtained in step 2) followed by adding the oryzanol; and cooling to room temperature followed by adding the berberine hydrochloride.

17. A method for treating diabetes, the method comprising: administering to a subject an anti-diabetic pharmaceutical composition according to claim 1, to thereby treat diabetes in the subject.

18. The method according to claim 17, wherein the beeswax is present in an amount of 2-10% by weight, and the sesame oil is present in an amount of 50-80% by weight, relative to the total weight of the pharmaceutical composition.

19. The method according to claim 17, wherein the oryzanol is present in an amount of 2-4% by weight, the berberine hydrochloride is present in an amount of 15-30% by weight, the beeswax is present in an amount of 3-6% by weight, and the sesame oil is present in an amount of 60-75% by weight, relative to the total weight of the pharmaceutical composition.

20. The method according to claim 17, wherein the weight ratio of beeswax to sesame oil is from 1:40 to 1:5.

21. The-method according to claim 17, wherein the weight ratio of oryzanol to berberine hydrochloride is 1:10.

22. The method according to claim 17, wherein the beeswax forms microcrystals and is homogeneously dispersed in the sesame oil, wherein the length of the microcrystals are from 0.1 to 100 μm.

23. The method according to claim 17, wherein the sesame oil is a machine-made sesame oil, ground sesame oil or common sesame oil.

* * * * *